US005554378A

United States Patent [19]
Uda et al.

[11] Patent Number: 5,554,378
[45] Date of Patent: Sep. 10, 1996

[54] PHARMACEUTICAL COMPOSITION AND ITS MUCOSAL USE

[75] Inventors: Yoshiaki Uda, Hyogo; Shigeyuki Takada, Osaka; Yukio Fujisawa, Hyogo, all of Japan

[73] Assignee: Takeda Chemical Industries, Ltd., Osaka, Japan

[21] Appl. No.: 379,114

[22] Filed: Jan. 27, 1995

Related U.S. Application Data

[63] Continuation of Ser. No. 47,064, Apr. 16, 1993, abandoned, which is a continuation of Ser. No. 753,075, Aug. 30, 1991, abandoned.

[30] Foreign Application Priority Data

Sep. 3, 1990 [JP] Japan .................................... 2-234303

[51] Int. Cl.[6] ...................................................... A61F 13/00

[52] U.S. Cl. ............................ 424/434; 424/43; 424/451; 514/944

[58] Field of Search .................................... 424/435, 434, 424/451, 43; 514/944

[56] References Cited

FOREIGN PATENT DOCUMENTS

| | | |
|---|---|---|
| 036145 | 9/1981 | European Pat. Off. . |
| 094157 | 11/1983 | European Pat. Off. . |
| 416505 | 3/1991 | European Pat. Off. . |
| 418626 | 3/1991 | European Pat. Off. . |
| 3018843 | 11/1980 | Germany . |
| 8606635 | 11/1986 | WIPO . |
| 90/03437 | 4/1990 | WIPO . |

OTHER PUBLICATIONS

J. Bacteriology, 150, 1482 (1982).
Microbiol. Immunol, 32, 1145 (1988).

*Primary Examiner*—D. Gabrielle Phelan
*Attorney, Agent, or Firm*—Foley & Lardner

[57] ABSTRACT

A pharmaceutical composition containing a physiologically active peptide or protein which is poorly absorbable through the gastrointestinal tract and heat-labile enterotoxin B subunit brings an increased absorbability of said peptide or protein into the mammalian body when administered through mucosa.

22 Claims, No Drawings

PHARMACEUTICAL COMPOSITION AND ITS MUCOSAL USE

This application is a continuation of U.S. application Ser. No. 08/047,064, filed Apr. 16, 1993, abandoned, which is a continuation of U.S. application Ser. No. 07/753,075, filed Aug. 30, 1991, now abandoned.

INDUSTRIAL APPLICATION

The present invention relates to a pharmaceutical composition comprising a physiologically active pepetide or protein and a heat-labile enterotoxin B subunit (hereinafter referred to briefly as LTB).

DESCRIPTION OF THE PRIOR ART

It is known that a highly hydrophilic medicinal compound with a low oil-water partition coefficient is either not absorbed or only sparingly absorbed from the gastrointestinal tract. Physiologically active peptides and proteins in general are not only strongly hydrophilic with low oil-water partition coefficients, but are hydrolized by enzymes in the gastrointestinal tract wall and are, therefore, hardly-absorbable from the gastrointestinal tract. Therefore, in order that sufficient drug efficacy may be ensured, such physiologically active peptides and proteins have heretofore been administered exclusively by the parenteral route. However, administration of drugs by injection is generally the job of professionals and, moreover, involves pain for the patients treated. Therefore, particularly for repeated administration, more convenient and handy pharmaceutical dosage forms have been demanded.

Meanwhile, LTB is the nontoxic moiety (B subunit) of the heat-labile enterotoxin (LT) produced by enterotoxigenic *Escherichia coli* organism. Being a simple protein which consists of 103 amino acid residues and has a molecular weight of 11,500, this subunit shows 83% homology with cholera toxin B subunit (CTB) at the amino acid level.

It has recently been demonstrated that CT and the B subunit of CT exhibit an adjuvant action in the mucosae of the intestinal tract and respiratory organs. Thus, it has been suggested that CT and CTB facilitate invasion of other antigens into the mucosa and potentiate the response of the local immune system of the mucosa in an early stage of sensitization. Since LTB is also considered to have similar activity, the application of LTB in the medicinal field can be a real possibility. In other words, LTB is expected to be of use as an adjuvant for enhancing the pharmacological activity of a physiologically active substance by assisting in the translocation of the substance through the mucosa.

SUMMARY OF THE INVENTION

The present invention provides a pharmaceutical preparation insuring increased bioavailability and, hence, enhanced pharmacologic action of physiologically active peptides and proteins which are poorly absorbable from the gastrointestinal tract. Thus, when LTB is used in combination with such a physiologically active peptide or protein, the absorption of the physiologically active peptide or protein administered by the pernasal route can be remarkably increased.

The present invention is directed to a pharmaceutical composition comprising a physiologically active peptide or protein and LTB.

Where the amino acids, fragment peptides and protective groups related to peptide are indicated by abbreviations in this specification, the abbreviations are all those adopted by IUPAC-IUB Commission of Biological Nomenclature or those in common use in this field of chemistry. Moreover, where any amino acid may occur as optical isomers, the L-compound is meant unless otherwise indicated.

The physiologically active peptide and physiologically active protein which can be employed in the present invention include, among others, a variety of peptides composed of at least 2 amino acid residues, to which sugars may optionally be coordinated. The pharmaceutically active peptides and proteins which can be used with advantage are those having high hydrophilicity and low oil-water partition coefficients. More particularly, there may be mentioned peptides and proteins with octanol-water partition coefficients not more than about 0.1. The molecular weights of such physiologically active peptides or proteins are preferably in the range of about 200 to 60000.

Specific examples of said physiologically active peptides or proteins are mentioned below.

Hormones:

L-pyroglutamyl-L-histidyl-L-prolinamide (thyrotropin releasing hormore; briefly TRH) and salts thereof, particularly the tartrate (Japanese Patent unexamined publication No. 50-121273), and its derivatives of the formula (I):

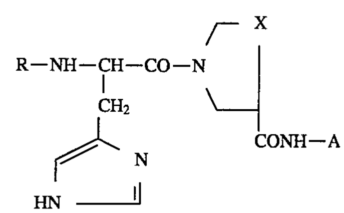

(I)

[wherein A means a hydrogen atom, a lower alkyl group of about 1 to 6 carbon atoms, an aralkyl group, such as a phenyl(lower)alkyl group, whose alkyl moiety has about 1 to 6 carbon atoms, a (lower)alkoxy(lower)alkyl group whose alkoxy and alkyl moieties respectively have about 1 to 6 carbon atoms, a hydroxy(lower)alkyl group containing about 1 to 6 carbon atoms or a lower alkoxy group of about 1 to 6 carbon atoms; R means 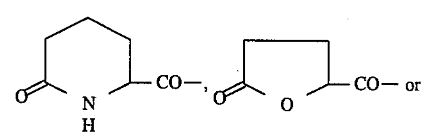 or 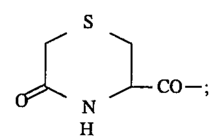 X means $—CH_2—$, $—CH_2CH_2—$ or $—S—$; R and the other constituent amino acid residues may respectively be optionally L-configured, D-configured or racemic, or salts thereof (Japanese Patent unexamined publication No. 52-116465). It should be understood that, in this specification, the compound of the following formula:

$$\text{(structure: pyroglutamyl-like ring)—O—CO—NH—CH(CH}_2\text{-imidazole)—CO—N(pyrrolidine-CONH}_2\text{)}$$

which is subsumed in the generic formula (I), is referred to as DN-1417.

As further examples of said physiologically active peptide, there may be mentioned luteinizing hormone-releasing hormone (briefly, LH-RH) and its homologs having similar activity, viz. peptides of formula (II):

$$(Pyr)Glu\text{-}R_1\text{-}Trp\text{-}Ser\text{-}R_2\text{-}R_3\text{-}R_4\text{-}Arg\text{-}Pro\text{-}R_5 \qquad (II)$$

[wherein $R_1$ means His Tyr, Trp or p-NH$_2$-Phe, $R^2$ means Tyr or Phe; $R_3$ means Gly or a D-amino acid residue; $R_4$ means Leu, Ile or Nle; $R_5$ means Gly-NH-$R_6$ ($R_6$ is H or a lower alkyl group of about 1 to 6 carbon atoms which may optionally have a hydroxyl group) or NH-$R_6$ ($R_6$ is as defined above)] and salts thereof [cf. U.S. Pat. Nos. 3,853, 837, 4,008,209 and 3,972,859; British Patent No. 1,423,083, and Proceedings of the National Academy of Sciences of the United States of America, 78, 6509–6512 (1981).]

Referring to the above formula (II), the D-amino acid residue $R_3$ includes, among others, α-D-amino acid residues containing up to 9 carbon atoms, such as D-Leu, Ile, Nle, Val, Nval, Abu, Phe, Phg, Ser, Thr, Met, Ala, Trp, α-Aibu, etc., and these residues may have appropriate protective groups (such as t-butyl, t-butoxy, t-butoxycarbonyl, etc.). Of course, acid salts and metal complexes of the peptide (II) can also be used likewise.

It should also be understood that the peptide of formula (II) wherein $R_1$=His; $R_2$=Tyr; $R_3$=D-Leu; $R_4$ =Leu; and $R_5$=NHCH$_2$—CH$_3$ is referred to herein as TAP-144.

Among further examples of said physiologically active peptide or protein having hormone activity are insulin, somatostatin, growth hormone, prolactin, adrenocorticotropic hormone (ACTH), melanocyte-stimulating hormone (MSH), thyroid-stimulating hormone (TSH), luteinizing hormone (LH), follicle-stimulating hormone (FSH), vasopressin, vasopressin derivatives [desmopressin, Folia Endocrinologica Japonica, 54 (5), 676–691 (1978), oxytocin, calcitonin, parathyroid hormone, glucagon, gastrin, secretin, pancreozymin, cholecystokinin, angiotensin, human placental lactogen, human chorionic gonadotropin (HCG), motilin, cerulein.

Analgesics:

enkephalin, enkephalin derivatives [U.S. Pat. No. 4,277, 394, European Patent Application Laid-open No. 31567], endorphin, dynorphin, kyotorphin and so on.

Lymphokines:

interferons (α, β and γ), interleukins (IL-1, -2, -3, -4, -5, -6, -7, -8, -9, -10, -11 etc.) and so on.

Hematopoietic growth factor:

granulocyte colony-stimulating factor, granulocyte macrophage colony-stimulating factor, macrophage colony-stimulating factor, erythropoietin, thymopoietin, thymosin and so on.

Enzymes:

urokinase, tissue plasminogen activator, kallikrein and so on.

Neuro transmitter:

bombesin, neurotensin, bradykinin, substance P

Growth factors:

nerve growth factor, epidermal growth factor, basofibroblast growth factor and so on.

The LTB to be employed in the present invention is the nontoxic moiety (B subunit) of a heat-labile enterotoxin (LT) which is produced by a toxigenic strain of *Escherichia coli*. Being a simple protein composed of 103 amino acid residues and having a molecular weight of 11,500, this subunit shows 83% homology with cholera toxin subunit B (CTB) at the amino acid level.

More particularly, the heat-labile enterotoxin (LT) is a kind of enterotoxin produced by toxigenic strains of *Escherichia coli* which are causative agents of diarrhrea. As the LT derived from entero toxigenic *E. coli* organisms, there are known LTp which is produced by the organisms causing diarrhea in domestic animals and LTh which is produced by the organisms causing diarrhea in man [Honda, T. et al.: Infection and Immunology, 34, 337 (1981); Tsuji, T. et al.: Infection and Immunology, 38, 444 (1982; and Geary, S. J. et al.: Infection and Immunology, 36, 215 (1982)].

LT is composed of A subunit having a molecular weight of 28,000 and B subunit having a molecular weight of 11,500 [Clements, J. D. & Finkelstein, R. A.: Infection and Immunology, 24, 760 (1979) and one molecule of LT consists of one molecule of A subunit and 5 molecules of B subunit, and it has been suggested that A subunit has activity as a toxin while B subunits are involved in the binding to the cell receptors [Gill, D. M. et al.: Infection and Immunology, 33, 677 (1981)].

The total base sequences of both A and B subunit genes of LTh and LTp have been determined [Dallas, W. S. & Falkow, S.: Nature, 277, 406 (1979); Yamamoto, T. & Yokota, T: J. Bacteriol., 155 728 (1983); Yamamoto, T. et al.: J. Biol. Chem., 259, 5037 (1984); Leong, J. et al., Infection and Immunology, 48, 73 (1985)] and based on these base sequences, it has been estimated that the A & B subunits of LTh and LTp are composed of 240 and 103 amino acid residues, respectively.

Because of the close similarity of LT to cholera toxin (briefly, CT) in physicochemical and immunological properties, although no detailed report is available on the mechanisms of action of LT in these mechanisms, too, LT is considered to be identical with CT.

Such LTB can be made available in quantities by the recombinant DNA technology. More particularly, LTB can be mass-produced by (1) preparing a region containing the LTB gene from a plasmid containing the cloned LT gene, (2) inserting this region into an expression vector containing one of $\lambda P_L$, $\lambda P_R$, trp, tac and T7 promotors in the normal direction to construct an LTB expression plasmid, (3) transforming *Escherichia coli* with said plasmid, and cultivating the transformant.

The pharmaceutical composition of the present invention can be manufactured by the per se known methods. For example, a pH adjusting agent, a preservative, a thickener (for example, natural gums, cellulose derivatives, acrylic polymers, vinyl polymers, etc.) and/or an excipient may be added in small quantities.

The pharmaceutical composition containing a physiologically active peptide or protein for mucosal delivery according to the invention can be made available in any of solid, liquid and semi-solid forms. In the case of a solid preparation, the above ingredients may be simply blended to provide a powdery composition or, if desired, may be made available as a lyophilized preparation. The particle size of such a preparation is preferably 5 to 250 microns. The liquid preparation is preferably an aqueous solution, an aqueous suspension or an oil suspension. The semi-solid preparation is preferably a hydrous or oily gel or ointment.

The recommended proportions of ingredients, in a solid preparation, may be as follows. Thus, the proportion of the physiologically active peptide or protein in the preparation is about 0.005 to 50 w/v % and preferably about 0.01 to 30 w/v %, and that of LTB is about 0.1 to 99.995 w/v % and preferably about 1 to 50 w/v %. In the liquid or semi-solid preparation, the proportion of the physiologically active peptide or protein is about 0.01 to 50 w/v % and preferably about 0.05 to 40 w/v %, and that of LTB is about 0.5 to 50 w/v % and preferably about 1 to 30 w/v %.

The solid preparation can be manufactured by the per se known methods. For example, a mixer is charged with an excipient and, then, a solution of the physiologically active peptide or protein and LTB in a small quantity of water is gradually added and kneaded. The mixture is then dried in vacuo at an appropriate temperature and pulverized to give the desired solid composition. As an alternative, a mixed powder of the physiologically active peptide or protein and LTB, plus an excipient where necessary, is thoroughly dissolved in water and, then, dehydrated by lyophilizing or spray-drying. The dried product is then pulverized to give the desired solid composition.

The excipient mentioned above includes, among others, glucose, mannitol, inositol, sucrose, lactose, fructose, starch, corn starch, microcrystalline cellulose, hydroxypropylcellulose, hydroxypropylmethylcellulose, polyvinylpyrrolidone and so on.

The liquid composition can be manufactured by the per se known methods. For example, an aqueous preparation for transnasal delivery can be provided by dissolving, suspending or emulsifying the physiologically active peptide or protein and LTB in water, a buffer solution or a hydrous medium. The oil suspension for transnasal delivery can be provided by suspending or emulsifying the physiologically active peptide or protein and LTB in an oleaginous base.

The buffer solution mentioned above includes, among others, Sörensen buffer [Ergeb. Physiol., 12, 393 (1912), Clark-Lubs buffer [J. Bact., 2, (1), 109 and 191 (1917)], MacIlvaine buffer [J. Biol. Chem., 49, 183 (1921)], Michaelis buffer [Die Wasserstoffinonenkonzentration, p. 186 (1914)], Kolthoff buffer [Biochem. Z., 179, 410 (1926)], and so on.

The oleaginous base includes, among others, sesame oil, olive oil, corn oil, soybean oil, cottonseed oil, peanut oil, lanolin, petroleum jelly, paraffin, Isopar, silicone oil, fatty acids containing 6 to 30 carbon atoms or the corresponding glycerol or alcohol esters, and so on. These bases may be used independently or in combination.

Regarding the method of producing said semi-solid preparation, a hydrous or oily gel or ointment can be manufactured by the per se known techniques. To manufacture a hydrous gel for transnasal delivery, for instance, an aqueous solution or suspension of LTB is first prepared and, where necessary, a pH adjusting agent, a preservative, etc. are added. This solution is divided into halves and a hydrous gel base is dissolved or dispersed in one of the halves and the solution or dispersion is appropriately warmed or cooled to give a stable gel. In the remaining half of said solution is dissolved the physiologically active peptide or protein. These two preparations are then combined and mixed thoroughly to provide a hydrous gel.

The pH adjustment in the above process can be made by adding an acid, a base, a buffer or the like in the course of pharmaceutical preparation. The acid which can be used for pH adjustment includes, among others, inorganic acids (e.g. hydrochloric acid, boric acid, phosphoric acid, carbonic acid, bicarbonic acid, etc.), amino acids, and organic acids (e.g. monocarboxylic acids, hydroxycarboxylic acids, polycarboxylic acids). The base may for example be sodium hydroxide, potassium hydroxide, sodium hydrogen carbonate, sodium carbonate or the like. The buffer may be any of those mentioned above.

The hydrous gel base include, among others, naturally-occurring gums (e.g. tragacanth gum, acacia gum, karaya gum, island moss, guar gum, xanthan gum, locust bean gum, etc.), cellulose derivatives (e.g. methylcellulose, carboxymethylcellulose, etc.), acrylic polymers (e.g. polyacrylic acid, polymethacrylic acid, etc.), vinyl polymers (e.g. polyvinylpyrrolidone, polyvinyl alcohol, polyvinyl methyl ether, carboxypolymethylene, etc.), synthetic polysaccharrides (e.g. polysucrose, polyglucose, polylactose, etc.), starch, dextrin, pectin, sodium alginate, proteins (gelatin, collagen, etc.) and so on. If desired, these bases may be used as an appropriate mixture.

The ointment for intransnasal delivery can be manufactured by dispersing LTB and said physiologically active peptide or protein uniformly in a heat-melted oleaginous base and allowing the dispersion to cool under constant stirring. The oleaginous base may be any of those mentioned hereinbefore.

The pharmaceutical composition for intranasal delivery may contain a preservative, e.g. p-hydroxybenzoic esters, phenols such as phenol, cresol, etc., alcohols such as chlorobutanol, phenylethyl alcohol, propylene glycol, etc., invert soaps such as benzalkonium chloride, benzethonium chloride, etc., and various acids and salts thereof such as benzoic acid, sorbic acid, dehydroacetic acid, sulfurous acid, etc. and salts thereof.

The methods for administration of the intranasal therapeutic system of the present invention may be as follows. To cite a typical method of administering a solid preparation, a capsule containing the powder is set on an exclusive spray device equipped with piercing needles to drill fine orifices at the upper and lower ends of the capsule and, then, a rubber balloon is deflated to force out the air and eject the powder into the nasal cavity.

A typical method of administering a liquid system comprises placing the liquid composition in a nasal applicator, spray container or the like which is suited for application of such liquid into the nasal cavity and dripping or spraying the composition into the nasal cavity.

An typical method of administering a semi-solid system comprises filling a tube with the composition, extemporaneously attaching an applicator to an opening of the tube and applying the composition directly into the nasal cavity or dispensing a predetermined amount of the composition into a nasal catheter or the like and administering it into the nasal cavity.

The dosage of the physiologically active peptide or protein is dependent on the kind of the peptide or protein, the disease condition to be controlled and other factors. As to the amount of the composition, it is about 5 mg to 100 mg in the case of a solid system, about 0.05 ml to 0.5 ml in the case of a liquid system, and about 50 mg to 500 mg in the case of a semi-solid system.

The present invention has the following characteristics.

1) A physiologically active peptide or protein which is hardly absorbed from the gastrointestinal tract can be administered by a method other than injection to achieve a high bioavailability.

2) A physiologically active peptide or protein can be easily administered without causing pain on administration.

3) Where multiple dosing is necessary, self-administration and, hence, home therapy are feasible.

4) Since LTB, used as an absorption promoting agent, is tasteless, odorless, sparingly toxic and sparingly irritating to the mucosa, the drug delivery system can be safely administered repeatedly.

EXAMPLES

The following experimental, reference and working examples are further illustrative of the invention. It should be understood that all percents (%) indicating concentrations are weight/volume percents (w/v %)

Experimental Example 1

Male SD rats (5 per group) weighing about 220 g were fasted for 16 hours. Under pentobarbital anaesthesia, the animals were prepared for intranasal therapy according to the procedure described in International Journal of Pharmaceutics 7, 317 (1981). Then, using a micropipet, 0.1 ml/kg of an insulin solution was directly administered into the nasal cavity and the blood was serially sampled from the tail vein for determination of blood glucose and insulin concentrations.

As said insulin solution, a solution of 10U of porcine insulin (about 0.38 mg) and 0 mg–5 mg of LThB (corresponding to 5%) in 0.1 ml of isotonic buffer (pH 7.4) was used.

The results are shown in Table 1. It is apparent from Table 1 that compared with the control (without LThB), the addition of LThB resulted in a marked fall of blood glucose level and the blood insulin concentration also indicates that the insulin administered was effectively absorbed from the nasal mucosa.

TABLE 1

| Absorption-promoting effect of LThB in intranasal delivery of insulin | | | |
|---|---|---|---|
| Time | Glucose (%)* | | Insulin (µU/ml) | |
| (hr) | No addition | 5% LThB | No addition | 5% LThB |
| 0.5 | 135.9 (10.5) | 115.3 (4.2) | 0.83 | 15.1 |
| 1.0 | 141.7 (8.6) | 97.2 (11.5) | 0.0 | 43.2 |
| 1.5 | 133.4 (11.2) | 92.9 (11.6) | 0.0 | 540.2 |
| 2.0 | 127.3 (9.1) | 92.2 (19.8) | 0.0 | 26.8 |
| 3.0 | 132.9 (11.4) | 110.9 (23.0) | 4.51 | 21.5 |
| 4.0 | 136.3 (13.5) | 113.2 (19.8) | 0.0 | 10.0 |

Insulin dose: 10 U/Kg, SD rats, 7W, ♂, 220 g
Plasma insulin level: EIA (GLAZYME Kit, Wako)
*% relative to glucose level before administration (mean ± SE, n = 5)

Reference Example 1

The transformant *E. coli* MM294 (DE3)/pLTB101 (IFO: IFO 14933; FRI; FERM BP-2583) obtained in accordance with Example 2 in the specification attached to Japanese Patent Application No. 1-227439, which was laid-opened as Japanese Patent unexamined Publication No. 3-187383 on Aug. 15, 1991, was inoculated into 40 ml of an LB medium containing 100 µg/ml of ampicillin and incubated in a 200 ml flask under shaking at 37° C. overnight. A 10 ml portion of the resulting culture was added to 200 ml of M9CA medium [Miller, Journal of Experiments in Molecular Genetics, 431–433, Cold Spring Harbor Laboratory, New York (1972)] containing 100 µg/ml of ampicillin and incubated in a 1-l flask at 37° C. for 3.5 hours. Then, isopropyl-thiogalactoside was added at a final concentration of 0.4 mM and the mixture was further incubated with shaking overnight. The culture broth was centrifuged using a Servall RC-5B centrifuge equipped with an SS34 rotor at 11,000 rpm (4° C.) for 20 minutes and the super natant was recovered. The same procedure was repeated to give a total of 5 liters of culture supernatant. This supernatant was passed through a CM-Toyopearl 650 M column (bed capacity 520 ml, ⌀/4.2×37.5 cm) equilibrated with 20 mM phosphate buffer (pH 6.0) and the column was washed with the same buffer. Elution was carried out with the same buffer supplemented with 0.5 M NaCl (12 ml/fraction). The LThB-containing fraction was subjected to SDS-PAGE and identified by silver staining and Western blotting with goat anticholera toxin antibody [Rist Biological Lab] and peroxidase-labeled rabbit anti-goat IgG antibody [Kappel]. The LThB fraction was concentrated by ultra-filtration to 5 ml and applied to a Sephacryl S-100HR column (bed capacity 130 ml, ⌀/1.6×65 cm) equilibrated with 10 mM phosphate buffer (pH 7.0) containing 0.85% NaCl. The LThB fraction was subjected to SDS-PAGE and identfied by silver staining and Western blotting. Since LThB was eluted in the position corresponding to a molecular weight of about 35,000, the possibility of trimer formation under the conditions was suggested. The LThB fractions were pooled and concentrated by ultrafiltration to give a purified sample (2.4 mg/ml).

Example 1

In 8 ml of an isotonic buffer (pH 7.4) is dissolved 5000 U (about 200 mg) of porcine insulin followed by addition of 50 mg of LThB and 20 mg of chlorobutanol. After complete dissolution, the solution is diluted with physiological saline to make 10 ml. This solution is put in a nasal applicator and about 0.1 ml is sprayed per dose.

Example 2

In 40 ml of purified water are dissolved 200 mg of DN-1417, 200 mg of mannitol and 200 mg of LThB and the solution is lyophilized. The dried product is pulverized to give a powder with a particle diameter of about 20 to 250 microns. A 30 mg portion of the powder is filled into a No. 4 hard gelation capsule. For administration, the capsule is set in an exclusive spray device equipped with needles for piercing the capsule and a rubber balloon for pressure delivery of air to thereby drill an orifice at either end of the capsule and the rubber balloon is then deflated to force out the air and the powder from the tip into the nasal cavity.

Example 3

In 16 ml of an isotonic buffer (pH 7.4) containing 0.12% of methylparaben and 0.01% of propylparaben are dissolved 1 g of LThB and 2 g of TAP-144 followed by addition of 200 mg of methylcellulose (Metolose 90SH400, Shin-Etsu Chemical). The mixture is stirred thoroughly to give a homogeneous viscous solution, which is then diluted with the same buffer to make a total of 20 g. A 100 mg portion of this preparation is filled into a nasal applicator and administered into the nasal cavity.

Example 4

Five-hundred milligrams of natural LH-RH (the peptide of general formula (II) wherein $R_1$=His, $R_2$=Tyr, $R_3$=Gly, $R_4$=Leu, $R_5$=Gly-$NH_2$) and 1 g of LThB are taken in a mortar, followed by addition of 1 g of lanolin melted by heating. After through mixing and dispersion, Miglyol 812

(Dynamit Nobel, West Germany) is gradually added with stirring to make a total of 10 g. This oil suspension is put in a container fitted with a dropping pipet and 0.1 g per dose is administered directly into the nasal cavity.

Example 5

In 1 ml of physiological saline are dissolved 50 mg of LThB and 100000 U of α-interferon (interferon derived from human leukocytes). This solution is put in a container fitted with a dropping pipet for nasal application and 0.1 ml of the solution is administered into the nasal cavity.

Example 6

In 10 ml of physiological saline are dissolved 2 mg of desmopressin and 500 mg of LThB followed by addition of 100 mg of methylcellulose. A 0.2 ml portion of the resulting viscous liquid is taken in an applicator and administered directly into the nasal cavity.

Example 7

In 20 ml of physiological saline are dissolved 1 g of enkephalin and 1 g of LThB. This solution is put in a spray-container and 0.2 ml per dose is sprayed into the nasal cavity.

Example 8

In 1 ml of physiological saline are dissolved 500 mg of active peptide portion (N terminus 34 portion) of parathyroid hormone (PTH) and 1 g of LThB. This solution is put in a spray-container and 0.2 ml per dose is sprayed into the nasal cavity.

What we claimed is:

1. A pharmaceutical composition, comprising a physical mixture of:

(a) a therapeutically effective amount of a physiologically active peptide or protein;

(b) heat-labile enterotoxin B subunit present in an amount effective to promote translocation of said physiologically active peptide or protein through nasal mucosa; and (c) a pharmaceutically acceptable carrier for mucosal administration, wherein said composition is a liquid or semi-solid preparation and the weight ratio of component (a) to component (b) is in the range of from 0.004 to 4.0.

2. A pharmaceutical composition as claimed in claim 1, wherein the composition is formed into a preparation for mucosal administration.

3. A pharmaceutical composition as claimed in claim 1, wherein the peptide or protein is hydrophilic.

4. A pharmaceutical composition as claimed in claim 1, wherein the peptide or protein is a hormone, lymphokine, enzyme, analgesic, hematopoietic growth factor, neuro transmitter or growth factor.

5. A pharmaceutical composition as claimed in claim 1, wherein the molecular weight of the peptide or protein is in the range of about 200 to 60,000.

6. A pharmaceutical composition as claimed in claim 1, wherein the octanol-water partition coefficient of the peptide or protein is not more than 0.1.

7. The pharmaceutical composition as claimed in claim 1, wherein said physiologically active peptide or protein is insulin.

8. The pharmaceutical composition as claimed in claim 1, wherein said physiologically active peptide or protein is thyrotropin releasing hormone or an analog thereof.

9. The pharmaceutical composition as claimed in claim 8, wherein said analog is DN-1417.

10. The pharmaceutical composition as claimed in claim 1, wherein said physiologically active peptide or protein is α-interferon.

11. The pharmaceutical composition as claimed in claim 1, wherein said physiologically active peptide or protein is enkephalin.

12. The pharmaceutical composition as claimed in claim 1, wherein said physiologically active peptide or protein is parathyroid hormone or an active fragment thereof.

13. The pharmaceutical composition as claimed in claim 12, wherein said active fragment is the N-terminal 34-amino acid portion of parathyroid hormone.

14. The pharmaceutical composition as claimed in claim 1, wherein said composition increases the bioavailability of the physiologically active peptide or protein, wherein the physiologically active peptide or protein is one that is not substantially absorbed from the gastrointestinal tract and is selected from the group consisting of insulin, thyrotropin releasing hormone or an analog thereof, α-interferon, enkephalin, and parathyroid hormone or an active fragment thereof.

15. A composition adapted for nasal administration, comprising: the pharmaceutical composition of claim 1, wherein said composition is in the form of a gel that can be applied to the nasal cavity for intimate contact with the nasal mucosa.

16. A composition adapted for nasal administration, comprising the pharmaceutical composition of claim 1, wherein said composition is in the form of a liquid capable of being sprayed into the nasal cavity for intimate contact with the nasal mucosa.

17. A composition adapted for nasal administration, comprising the pharmaceutical composition of claim 1, wherein said composition is in the form of a powder contained in a capsule, which is capable of spraying the powder into the nasal cavity for intimate contact with the nasal mucosa.

18. A method of administering a physiologically active peptide or protein through the nasal cavity of a subject in need thereof, comprising the step of providing to the nasal mucosa of said subject a pharmaceutical composition comprising a physical mixture of:

(a) a therapeutically effective amount of a physiologically active peptide or protein;

(b) heat-labile enterotoxin B subunit present in an amount effective to promote translocation of said physiologically active peptide or protein through nasal mucosa; and (c) a pharmaceutically acceptable carrier for mueosal administration, wherein said pharmaceutical composition is a liquid or semi-solid preparation and the weight ratio of component (a) to component (b) is in the range of from 0.004 to 4.0.

19. A method as claimed in claim 18, wherein the pharmaceutical composition is a uniform mixture in dosage form.

20. A method as claimed in claim 18, wherein the peptide or protein is a hormone lymphokie, enzyme, analgesic, hematopoietic growth factor, neuro transmitter or growth factor.

21. The method of claim 18, wherein the molecular weight of the peptide or protein is in the range of about 200 to 60,000.

22. The method of claim 18, wherein the octanol-water partition coefficient of the peptide or protein is not more than 0.1.

* * * * *